United States Patent [19]
Foley et al.

[11] Patent Number: 5,149,417
[45] Date of Patent: Sep. 22, 1992

[54] GEL ELECTROPHORESIS CASSETTE

[75] Inventors: Brian D. Foley, Westford; John Iovaine, Melrose, both of Mass.

[73] Assignee: Millipore Corporation, Bedford, Mass.

[21] Appl. No.: 759,263

[22] Filed: Sep. 13, 1991

[51] Int. Cl.$^5$ .................. B01D 61/42; C25D 13/00
[52] U.S. Cl. .............................................. 204/299 R
[58] Field of Search .................... 204/182.8, 299 R

[56] References Cited
U.S. PATENT DOCUMENTS
4,929,329  5/1990  Danby et al. .................. 204/299 R Primary Examiner—T. Tung
Assistant Examiner—Caroline Koestner
Attorney, Agent, or Firm—Andrew T. Karnakis; Paul J. Cook

[57] ABSTRACT

A gel electrophoresis cassette is provided having two plates and two spacers between the plates. The spacers are positioned slightly inward of the plate edges to form small edge spaces. A soft adhesive is positioned within the small edge spaces and, subsequent to electrophoresis, the adhesive can be easily removed from the small spaces. The plates and separators then can be separated manually.

9 Claims, 1 Drawing Sheet

U.S. Patent     Sep. 22, 1992     5,149,417
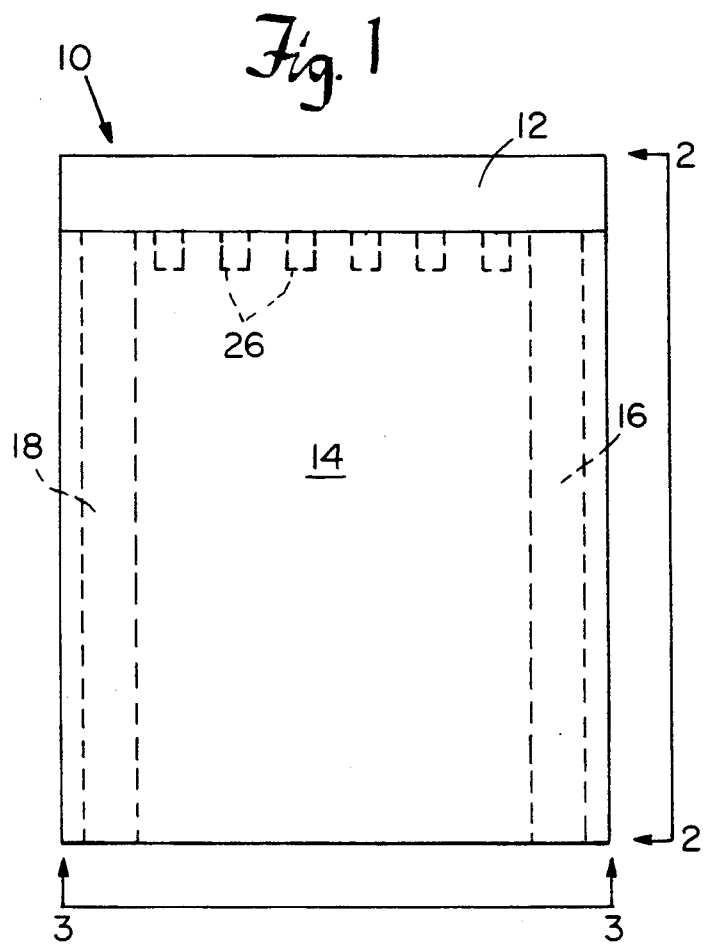
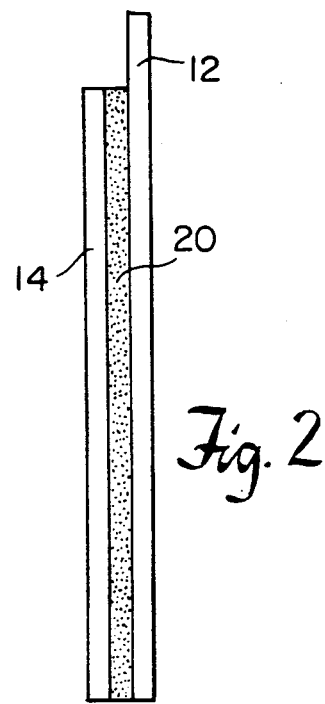
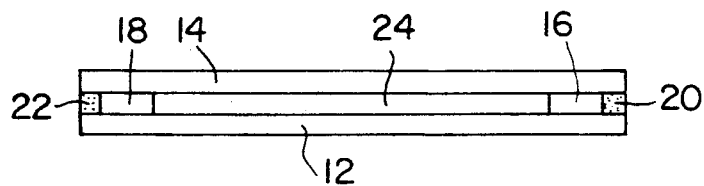

GEL ELECTROPHORESIS CASSETTE

BACKGROUND OF THE INVENTION

This invention relates to an electrophoresis cassette useful for conducting gel electrophoresis separations.

Electrophoresis is the resolution of a complex mixture of macromolecules on the basis of charge and/or size under the influence of an electric field and is a primary tool in analytical chemistry, used to separate complex mixtures of molecules such as proteins into their individual components. Electrophoretic analysis is based upon the fact that each molecule is characterized by a particular electrophoretic mobility under a given set of conditions. Macromolecules will migrate within a voltage gradient according to their net charge and will reach equilibrium at their isoelectric point at which their net mobility will be zero. For example, many proteins exhibit a net negative charge which is affected by the surrounding pH. When a mixture of proteins is placed in a support medium, such as a buffered gel, which is subjected to a voltage gradient, each component is caused to migrate through the support medium at its characteristic rate for that set of conditions. Electrophoretic mobility is a function of net charge, molecular weight, shape and a number of other factors which are controlled by experimental conditions.

It is common practice to conduct electrophoresis in a buffered gel positioned between two flat plates, usually transparent glass or plastic and separators between the plates which provide essential support for the gel. In order to provide accurate sample resolution, it is necessary that the gel composition be uniform and that the gel thickness be uniform. These conditions are necessary in order to avoid factors which affect molecular electrophoretic mobility other than the characteristics of the molecules being separated.

Presently, a cassette is produced wherein a void volume is formed between two plates separated by two separators. A suitable separation gel medium such as agarose or a polyacrylamide is poured, in liquid form, into the void volume and allowed to gel therein. During formation of the gel, the two plates are compressed to the separators with tape or clamps to prevent leakage of the gel material from the void volume and to assure a uniform distance between the plates, which, in turn, assures a uniform gel thickness.

In use, the cassette is positioned between two buffer solutions after the sample or samples have been placed on one gel surface. A voltage is applied between the buffers which causes the samples to migrate within the gel. Upon completion of sample preparation, the gel is separated from the plates for analysis. When using tape to secure the plates in position, it is difficult to apply it to the cassette consistently because the tape can fold, stretch or break. In addition, many of the adhesives used with tapes degrade with time. These conditions can cause poor sample separations to occur. Clamping systems that use bolts require the use of tools such as screw drivers and wrenches to disassemble the cassettes and include several components that can be lost or damaged. Clamping systems using spring mechanisms have problems with uneven sealing due to uneven spring pressures on components that are not perfectly flat.

Accordingly, it would be desirable to provide a cassette for gel electrophoresis that does not introduce anomolies in the separation process, is easy to disassemble without fixtures, minimizes the number of components forming the casettes and minimizes gel damage during disassembly.

SUMMARY OF THE INVENTION

The present invention provides a gel electrophoresis cassette comprising two plates and two separators postioned between the plates. The separators are retained in position by means of an adhesive which extends the length of the separator. The adhesive is compatible with electrophoresis buffer and, when cured, is soft so that it can be easily removed from between the plates so that the plates can be separated from the gel upon completion of electrophoresis. Subsequent to gel electrophoresis utilizing the cassette, the adhesive is removed with a tool that fits between the plates. The plates then can be manually removed from contact with the gel since the bond between (a) the adhesive and (b) the plates and separators has been broken by the tool used.

BRIEF DESCRIPTION OF THE DRAWINGS

FIG. 1 is a plan view of the casette of this invention.
FIG. 2 is a side view of the cassette of FIG. 1.
FIG. 3 is a bottom view of the cassette of FIG. 1.

DESCRIPTION OF SPECIFIC EMBODIMENTS

Referring to Figures the gel electrophoresis cassette of this invention 10 is shown. FIG. 2 is a side view of the cassette 10 of FIG. 1 in the direction of arrow 2. FIG. 3 is a bottom view of the cassette 10 of FIG. 1 in the direction of arrow 3. The cassette 10 is comprised of a back plate 12, a front plate 14 and two spacers 16 and 18. The spacers 16 and 18 and the plates 12 and 14 are retained together by means of adhesive strips 20 and 22 positioned in the small edge spoils defined by the plates 12 and 14 and by one spacer 16 or 18. The electrophoresis gel 24 is positioned within the void volume defined by the plates 12 and 14 and the spacers 16 and 18. The gel 24 is provided with wells 26 which are molded into the gel 24 when it is formed in the void volume. The wells 26 house the samples which are to be sepaerated within the gel 24.

When it is desired to separate the plates 12 and 14, a projection is embedded into the adhesive strips 20 and 22 so that the adherence of the plate 12 to the plate 14 is not maintained. This permits manual separation of the plates and spacer so that the gel can be recovered and the separated samples analyzed.

The adhesive, preferably is a room temperature vulcanizable (RTV) adhesive or ultraviolet light (UV) curable adhesive. Representative suitable adhesives include silicone or epoxy based adhesives since these adhesives are relatively soft when cured and can be easily torn with a tool having a projection which extends into the small edge spaces filled by the adhesive. The adhesives should have a Durometer (Shore A) of between about 45 and 70, preferably between about 55 and 65. In addition, these adhesives are easily applied, remain in place during curing and remain integral with the cassettes for long period, typically greater than one year. In addition, these adhesives are compatible with the buffers used in electrophoresis.

What is claimed is:

1. A cassette for conducting electrophoresis which comprises:

a first flat plate having two side edges substantially parallel to each other, a second flat plate having two side edges substantially parallel to each other, a first spacer positioned inward slightly away from a side edge of said first flat plate and away from a side edge of said second flat plate to form a first small space between said plates, a second spacer positioned inward slightly away from a side edge of said first flat plate and away from a side edge of said second flat plate to form a second small space between said plates, a space adapted to retain a gel defined by said first flat plate, said second flat plate, said first spacer and said second spacer, and a soft adhesive positioned within said first small space and said second small space and having a Durometer (Shore A) of between about 45 and 70, thereby to effect adhesion between (a) said first plate, said second plate and said first spacer and (b) said first plate, said second plate and said second spacer.

2. The cassette of claim 1 wherein said adhesive is a silicone based adhesive.

3. The cassette of claim 1 wherein said adhesive is an epoxy based adhesive.

4. The cassette of claim 1 wherein said space is filled with an electrophoresis gel.

5. The cassette of claim 4 wherein a plurality of wells extend from a surface of said gel and into said gel.

6. The cassette of claim 5 wherein said adhesive is an epoxy based adhesive.

7. The cassette of claim 5 wherein said adhesive is a silicone based adhesive.

8. The cassette of claim 4 wherein said adhesive is a silicone based adhesive.

9. The cassette of claim 4 wherein said adhesive is an epoxy based adhesive.

* * * * *